United States Patent
Lawrenson et al.

(10) Patent No.: US 12,089,633 B2
(45) Date of Patent: Sep. 17, 2024

(54) ELECTRONIC CIGARETTE

(71) Applicant: JT International S.A., Geneva (CH)

(72) Inventors: Matthew John Lawrenson, Chesterfield, MO (US); Timothy Giles Beard, Cambridge (GB); Christopher Wright, Lausanne (CH)

(73) Assignee: JT International S.A. (CH)

( * ) Notice: Subject to any disclaimer, the term of this patent is extended or adjusted under 35 U.S.C. 154(b) by 713 days.

(21) Appl. No.: 17/288,756

(22) PCT Filed: Dec. 18, 2019

(86) PCT No.: PCT/EP2019/085949
§ 371 (c)(1),
(2) Date: Apr. 26, 2021

(87) PCT Pub. No.: WO2020/127482
PCT Pub. Date: Jun. 25, 2020

(65) Prior Publication Data
US 2021/0401038 A1    Dec. 30, 2021

(30) Foreign Application Priority Data

Dec. 19, 2018   (EP) .................................... 18213931

(51) Int. Cl.
*A24F 40/30*       (2020.01)
*A24F 40/10*       (2020.01)
(Continued)

(52) U.S. Cl.
CPC .............. *A24F 40/30* (2020.01); *A24F 40/10* (2020.01); *A24F 40/42* (2020.01); *A24F 40/46* (2020.01); *A24F 40/485* (2020.01); *A24F 40/50* (2020.01)

(58) Field of Classification Search
CPC ........ A24F 40/30; A24F 40/485; A24F 40/10; A24F 40/46; A24F 40/42; A24F 40/50
(Continued)

(56) References Cited

U.S. PATENT DOCUMENTS 3,745,635 A * 7/1973 Harris ................. B29C 66/8242
                                                     29/731
5,269,327 A * 12/1993 Counts .................... A24F 40/30
                                                    131/194
(Continued)

FOREIGN PATENT DOCUMENTS

CN      203378558 U    1/2014
WO      2013152873 A1  10/2013
(Continued)

OTHER PUBLICATIONS

International Search Report for Application No. PCT/EP2019/085949, dated Apr. 3, 2020, 4 pages.

*Primary Examiner* — Harshad C Patel
(74) *Attorney, Agent, or Firm* — Lerner David LLP

(57) ABSTRACT

An electronic cigarette includes a plurality of liquid reservoirs configured to store different liquids, each of the liquid reservoirs being fluidically coupled to a heater, a memory configured to store at least one program defining which heater is activated and a duration of time for the activation, a timer configured to regulate the time during which each heater is activated, a controller configured to selectively control the activation of each heater according to the at least one program on the memory, wherein the electronic cigarette is configured to produce a vapour with variations in its composition over time during the course of a vaping session.

17 Claims, 7 Drawing Sheets

(51) Int. Cl.
*A24F 40/42* (2020.01)
*A24F 40/46* (2020.01)
*A24F 40/485* (2020.01)
*A24F 40/50* (2020.01)

(58) Field of Classification Search
USPC .......................................................... 131/329
See application file for complete search history.

(56) References Cited

U.S. PATENT DOCUMENTS

| | | | |
|---|---|---|---|
| 9,999,247 B2 * | 6/2018 | Ruscio | ................... A24F 40/46 |
| 2001/0020450 A1 * | 9/2001 | Vieira | ................. A01M 1/2077 |
| | | | 122/366 |
| 2014/0301721 A1 * | 10/2014 | Ruscio | ................... A24F 40/46 |
| | | | 392/386 |
| 2017/0042230 A1 | 2/2017 | Cameron | |
| 2017/0258140 A1 * | 9/2017 | Rostami | ................ A24F 40/485 |

FOREIGN PATENT DOCUMENTS

| | | |
|---|---|---|
| WO | 2015038981 A2 | 3/2015 |
| WO | 2016145072 A1 | 9/2016 |
| WO | 2018177826 A1 | 10/2018 |

* cited by examiner

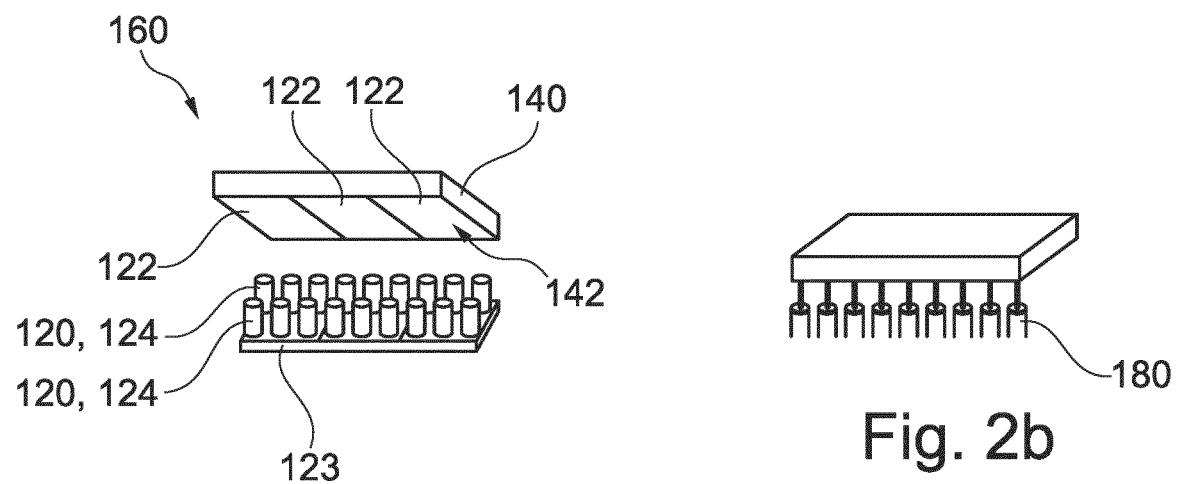
Fig. 2a
Fig. 2b
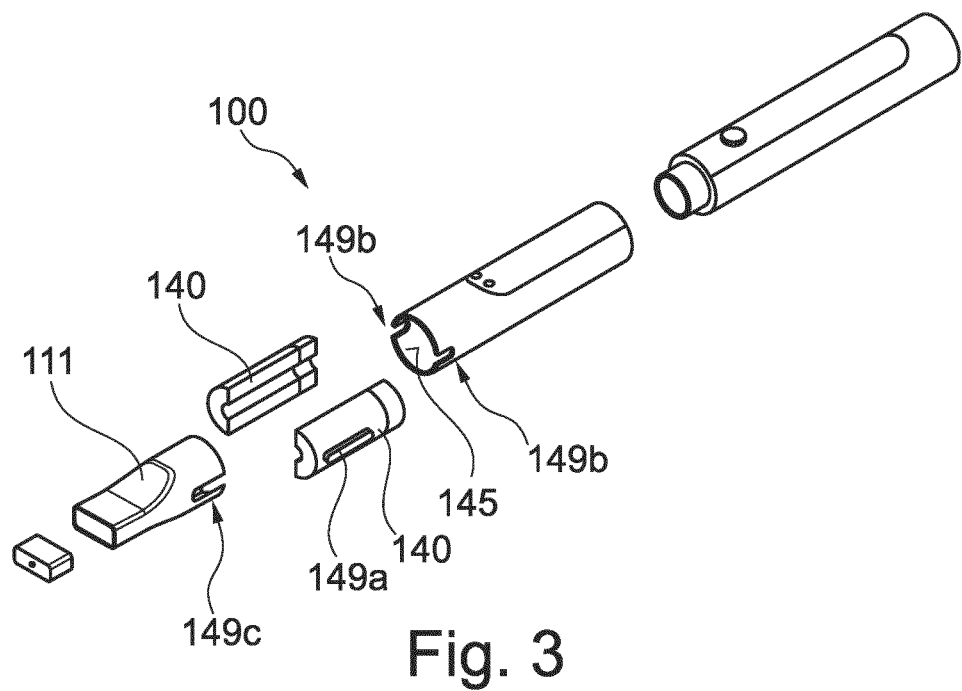
Fig. 3

ELECTRONIC CIGARETTE

CROSS-REFERENCE TO RELATED APPLICATIONS

The present application is a national phase entry under 35 U.S.C. § 371 of International Application No. PCT/EP2019/085949, filed Dec. 18, 2019, published in English, which claims priority to European Application No. 18213931.1 filed Dec. 19, 2018, the disclosures of which are incorporated herein by reference.

FIELD OF THE INVENTION

The present invention relates to an electronic cigarette, in particular to an electronic cigarette in which a vapour is generated from an aerosol-generating liquid.

BACKGROUND OF THE INVENTION

The term electronic cigarette, or e-cigarette, is usually applied to a handheld electronic device that simulates the feeling or experience of smoking tobacco in a traditional cigarette. Electronic cigarettes work by heating an aerosol-generating liquid to the point of vaporisation to generate the aerosol, commonly called a vapour, that is then inhaled by the user.

Accordingly, using e-cigarettes is sometimes also referred to as "vaping". The aerosol-generating liquid in the electronic cigarette is sometimes called an "e-liquid" and usually comprises nicotine, propylene glycol, glycerine and flavourings.

Most e-cigarettes contain a reservoir with a single e-liquid flavour. This reservoir may be disposable, in the form of a cartridge containing e-liquid for one or several vaping sessions, and may incorporate a heating element in the disposable part. Alternatively, the tank may be user-refillable and configured as a permanent part of the electronic cigarette.

WO2013/152873 discloses an electronic cigarette having a plurality of liquid reservoirs and mixing means enabling the user to set a desired flavour mix. However, to change the flavour of the vapour, the user needs to manually change the settings. It can be difficult for the user to calibrate the device and create a desired setting of the flavour by himself and get a satisfying result.

SUMMARY OF THE INVENTION

In view of the above, it is an object of the present invention to provide an electronic cigarette that provides easy and accurate flavour mixing capabilities.

Electronic cigarettes also have the drawback over conventional cigarettes that the smoking ritual does not have a clear start and end. For conventional cigarettes, the start and end are defined by the length of the cigarette and the visual changes of the cigarette during smoking. It would therefore be an advantage to provide an electronic cigarette capable of providing a defined smoking ritual for the user and assists the user to correctly operate the device, e.g. informing the user when the electronic cigarette can be turned off after smoking.

Further, electronic cigarettes generally comprise components that are multi-use and thus usually restrict the user to certain types of flavours or flavour combinations compared to classic ready-made tobacco cigarettes where the user can at any time buy a disposable pack having new flavours.

According to a first aspect, an electronic cigarette is provided comprising:
a plurality of liquid reservoirs configured to store different liquids,
at least one heater, wherein each of the liquid reservoirs is fluidically coupled to the at least one heater,
a regulating arrangement configured to selectively enable the delivery of liquid from at least one liquid reservoir to the at least one heater,
a memory configured to store at least one program defining which liquid reservoir is enabled for liquid delivery to the at least one heater and a duration of time for the activation,
a controller configured to selectively control the enablement of each liquid reservoir according to the at least one program on the memory, a timer configured to regulate the time during which each liquid reservoir is enabled,
whereby the electronic cigarette is configured to produce a vapour with variations in its composition over time, preferably during the course of a vaping session.

The liquid reservoirs may be an integral part of the electronic cigarette such that they can be refilled and re-used. The liquid reservoirs may also be part of a consumable, such as a cartridge, that can be inserted into the electronic cigarette and that can be extracted from the electronic cigarette when at least one liquid reservoir or all of the liquid reservoirs are depleted. The liquid reservoirs may also be individually insertable into, and extractable from the electronic cigarette such that a user can insert a desired variety and composition of different liquid reservoirs into the electronic cigarette, thus enabling new compositions of the vapour. Each of such individually insertable and extractable liquid reservoirs may also function as a cartridge itself, and the electronic cigarette may be configured to receive multiple cartridges.

The term "cartridge" is used herein in a broad sense and is not supposed to restrict the exterior form of the consumable; rather, it is meant to designate a consumable that may be inserted at least partially, preferably completely, into the electronic cigarette, or that may be attachable to the electronic cigarette, and which may be removed from the electronic cigarette when that is desired, especially when one or more of the liquid reservoirs of the cartridge are depleted. Many embodiments will herein be described with respect to a cartridge. It should be understood, however, that also any other suitable type of consumable may be substituted for a cartridge in each case.

The variations in vapour composition may be a result of a liquid with varying liquid composition being vaporised and/or may be a result of a varying mixture of vapours created by different liquids which are vaporised at the same time.

The timer may be configured to measure an amount of time in seconds (or milliseconds or the like) and/or in a number of puffs.

According to a second aspect of the invention, a cartridge for an electronic cigarette is provided, the cartridge having a plurality of liquid reservoirs formed as separate compartments, wherein the cartridge further comprises a memory configured to store at least one program, wherein the program comprises instructions which enable a regulating arrangement in the electronic cigarette to produce a vapor with variations in its composition over time, preferably during the course of a vaping session.

According to a third aspect of the present invention, an electronic cigarette is provided which comprises: a plurality of cartridges, each having at least one liquid reservoir; and a main body having a cartridge seating that is configured to be releasably connectable to the plurality of cartridges;

the main body having an elongate shape and comprising a power supply and a regulating arrangement configured to selectively enable the delivery of liquid from at least one liquid reservoir to at least one heater of the electronic cigarette;

wherein the cartridge seating comprises a tubular receiving cavity; and wherein the plurality of cartridges are shaped such that a combined axial cross-section of the plurality of cartridges corresponds to an axial cross-section of the tubular receiving cavity.

According to a fourth aspect of the present invention, a consumable for an electronic cigarette is provided, the consumable comprising a heater and a liquid reservoir, wherein the housing has an axial cross-section the shape of a fraction of a circle, preferably a half-circle.

Further advantageous variants and modifications will be explained in the following with respect to the dependent claims as well as the description in combination with the figures.

In some advantageous embodiments, the regulating arrangement comprises at least one valve. In this way, the transfer of liquid can be controlled more precisely.

In some advantageous embodiments, the valve further comprises a valve body configured to enable and modify the liquid supply from a plurality of liquid reservoirs. This allows more flexibility in combining liquids to achieve different flavor combinations.

In some advantageous embodiments, the valve is a rotary body having a plurality of channels configured to be selectively aligned and selectively disaligned to (or: with) outlets from the liquid reservoirs.

In some advantageous embodiments, the regulating arrangement comprises a plurality of valves. In some of those embodiments, each valve is configured to regulate the flow of liquid from each liquid reservoir.

In some advantageous embodiments, the regulating arrangement comprises a plurality of heaters and each of the liquid reservoirs is fluidically coupled to the at least one heater. In this way, each heater may be specifically adapted, or controlled, to heat and vaporize a specific liquid, taking into account e.g. different vaporizing temperatures and the like.

In some advantageous embodiments, each liquid reservoir is connected to a dedicated heater. In other words, the electronic cigarette may comprise as many heaters as it comprises liquid reservoirs. This allows to individually heat each liquid from each liquid reservoir to an individual, optimal vaping temperature and/or to heat (or not) the liquid from each liquid reservoir independently. If the liquid reservoirs are external to the electronic cigarette, i.e. arranged on a consumable, then the electronic cigarette preferably comprises as many heaters as it comprises fluid transfer elements that are configured for conducting aerosol-generating liquid from the liquid reservoirs to the heaters, and each fluid transfer element may be fluidically connected to a respective dedicated heater and vice versa.

In some advantageous embodiments, the controller is configured to selectively control the activation of each heater according to the at least one program on the memory.

In some advantageous embodiments, the timer is configured to regulate the time during which each heater is activated.

In some advantageous embodiments, at least two heaters can be activated at separate times. This enables to more precisely create vapour compositions varying over time, e.g. by first activating a first heater and then, with a temporal offset, activate a second heater. Particularly, it enables to blend flavours and to phase over from one flavour to another without a sharp break or contrast.

In some advantageous embodiments, at least two heaters can be activated at the same time. This allows to creating complex vapour compositions from at least two different liquids from at least two different liquid reservoirs at the same time.

In some advantageous embodiments, at least two of the liquid reservoirs comprise an active ingredient such as nicotine. In some advantageous embodiments, the liquid reservoirs comprise liquids of different strength or concentration of the active ingredient, e.g. different nicotine strength. In some advantageous embodiments, at least two of the liquid reservoirs comprise liquids with identical composition with the exception of their respective strength or concentration of the same active ingredient, e.g. nicotine. Preferably, the variation in vapour composition over time includes, or consists of, a variation in strength or concentration of the active ingredient, e.g. in nicotine strength. In this way, the electronic cigarette may be used to precisely dose a drug, or an active ingredient of a drug, according to a predetermined dosage regime.

In some advantageous embodiments, the liquid reservoirs comprise liquids of at least two different flavours. Preferably, the variation in vapour composition (e.g. according to at least one program stored in the memory) includes, or consists of, a variation in flavour.

In some advantageous embodiments, at least one liquid reservoir comprises a liquid that does not have a flavour or is flavour-neutral (i.e. flavourless). Such a flavour-neutral liquid may be used to dilute an otherwise too strong flavour, or to efficiently carry an active ingredient e.g. of a drug which is thus addable to any possible flavour composition that can be provided by the electronic cigarette.

In some advantageous embodiments, the program contains different heating profiles in order to achieve different flavour strengths and/or different strengths of concentrations of an active ingredient.

In some advantageous embodiments, the liquid reservoirs are provided on a support forming a unitary cartridge and the at least one program is located on a memory on the cartridge.

In some advantageous embodiments, the at least one program is located on memory on a main body of the electronic cigarette.

In some advantageous embodiments, the at least one program contains different heating profiles in order to achieve different flavour strengths. Such a heating profile may comprise a sequence of heaters to be activated for specific durations and with specific heating temperatures.

In some advantageous embodiments, the at least one program comprises a set of different heating profiles, and each heating profile is linked to a specific composition and/or flavour.

In some advantageous embodiments, the program can be created and/or adapted by the user, e.g. using a user interface of the electronic cigarette, or an app running on a mobile device connectable to the electronic cigarette via a wireless or wire bound interface.

In some advantageous embodiments, the flavour combination and timing (e.g. of at least one program) can be set by the user.

In some advantageous embodiments, the at least one program is based on a sensor input, for example on the input of a particle sensor such as a food molecule sensor. In this way, the vapour composition can automatically be set based on e.g. a previous consumption of a user and/or on a chemical balance (e.g. acidic/basic) within the mouth of the user. For example, some components of the vapour may, in combination with certain molecules or a certain chemical balance, taste especially good or especially bad or might even induce nausea or other undesired effects. In such cases, the sensor input may be used to automatically adjust the vapour composition to at least compensate such an effect.

The sensor may also be a sensor configured to detect a user's circadian rhythm, and the controller may be configured to adapt and/or choose a program based on the detected circadian rhythm, preferably based in addition on a current time and/or current date.

In some advantageous embodiments, the program comprises a set of different heating profiles. Each heating profile may be linked to a specific composition and/or flavor. As has been discussed in the foregoing, specific vapour compositions may require specific heating profiles to optimize taste and/or delivery of an active ingredient.

In some advantageous embodiments, the heaters comprise, or are in the form of, needles with a capillary tube. The needles may be configured to function as fluid transfer members by capillary effect.

In some advantageous embodiments, the heaters (either collectively or each individually, or groups of heaters individually) are moveable between a retracted position and an extended position. This is in particular advantageous if the heaters are formed as, or formed as comprising, piercing members such as needles, since then the heaters may be moved to the extended position to pierce a sealing or packaging on a consumable to access the aerosol-generating liquids stored therein.

In some advantageous embodiments of the cartridge according to the second aspect of the present invention, the cartridge further comprises a plurality of heaters each connected to a dedicated liquid reservoir.

In some advantageous embodiments of the electronic cigarette according to the third aspect of the present invention, the combined axial cross-section of the plurality of cartridges is essentially, or exactly, equal to the axial cross-section of the tubular receiving cavity.

In some advantageous embodiments, the cartridge seating comprises a plurality of electrical connectors configured to connect to the atomizer assembly.

In some advantageous embodiments, the cartridge comprises an integrated atomizer comprising a heater and a fluid transfer element, and the cartridge seating comprises a plurality of electrical connections configured to connect to each cartridge.

In some advantageous embodiments, the electrical connections are configured as resilient contacts.

In some advantageous embodiments, the atomizer assembly comprises a plurality of piercing members.

In some advantageous embodiments, the cartridge seating further comprises a piercing member configured as a fluid transfer element. Preferably, the fluid transfer element is a porous member.

In some advantageous embodiments, the cartridge seating comprises guiding elements configured to position the cartridges in an angular position such that the cartridges are aligned with connectors in the cartridge seating.

In some advantageous embodiments, the elongate body further comprises user controls configured to enable the user to control the amount of liquid that is used from each liquid reservoir to generate the aerosol.

In some advantageous embodiments, the user controls are selected from the group comprising a scroll wheel, a set of two buttons, a rocker button, and a rotary dial.

In some advantageous embodiments, the user control is a rotary dial that is located at a distal end of the elongate body opposite to a mouthpiece, or mouthpiece connector, of the electronic cigarette.

In some advantageous embodiments, the electronic cigarette further comprises a display, wherein the display is configured to display the proportion of flavors in the vapor.

In some advantageous embodiments, the display is a light source (e.g. an RGB LED) configured to indicate the flavor or nicotine strength by different color or by different intensity of color.

In some advantageous embodiments, the display is located at an end portion of the main body, distal to the cartridge seating and the rotary dial is arranged around the end portions of the distal end.

In some advantageous embodiments, at least one of the liquid reservoirs comprises a flavorant.

In some advantageous embodiments, at least two liquid reservoirs comprise aerosol producing compositions of different nicotine strengths.

In some advantageous embodiments, one of the liquid reservoirs comprises an aerosol producing composition without nicotine.

In some advantageous embodiments, the electronic cigarette further comprises a sleeve configured to enclose the liquid reservoirs and hold them together.

In some advantageous embodiments, the sleeve further comprises a mouthpiece portion or a mouthpiece connector.

In some advantageous embodiments of the consumable according to the second aspect or the fourth aspect, the liquid reservoir comprises a vaporization chamber, a first portion of a vapor outlet channel from the vaporization chamber and a groove, wherein the grooves of at least two liquid reservoirs form a vapor outlet channel.

In some advantageous embodiments, the consumables comprise inter-locking connectors.

In some advantageous embodiments, the consumables comprises an airflow diverter, configured to generate turbulence in the vapor channel.

The invention also provides a cartridge assembly for an electronic cigarette, the cartridge assembly having a plurality of liquid reservoirs formed as separate compartments, wherein the cartridge further comprises a memory configured to store at least one program, wherein the program comprises instructions which enable a regulating arrangement in the electronic cigarette to produce a vapour with variations in its composition over time, preferably during the course of a vaping session.

BRIEF DESCRIPTION OF THE DRAWINGS

For a more complete understanding of the invention and the advantages thereof, exemplary embodiments of the invention are explained in more detail in the following description with reference to the accompanying drawing figures, in which like reference characters designate like parts and in which:

FIG. 1b shows a schematic cross-sectional view of the electronic cigarette of FIG. 1a;

FIG. 2a shows a schematic view of part of an electronic cigarette according to another embodiment of the present invention;

FIG. 2b shows a schematic view of part of an electronic cigarette according to yet another embodiment of the present invention;

FIG. 3 shows a schematic exploded view of part of an electronic cigarette according to still another embodiment of the present invention;

The accompanying drawings are included to provide a further understanding of the present invention and are incorporated in and constitute a part of this specification. The drawings illustrate particular embodiments of the invention and together with the description serve to explain the principles of the invention. Other embodiments of the invention and many of the attendant advantages of the invention will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will be understood that the terms and expressions used in the present specification have the ordinary meaning as is accorded to such terms and expressions with respect to their corresponding respective areas of inquiry and study, except where specific meanings have otherwise been set forth herein.

DETAILED DESCRIPTION OF EMBODIMENTS

Figure 1A:
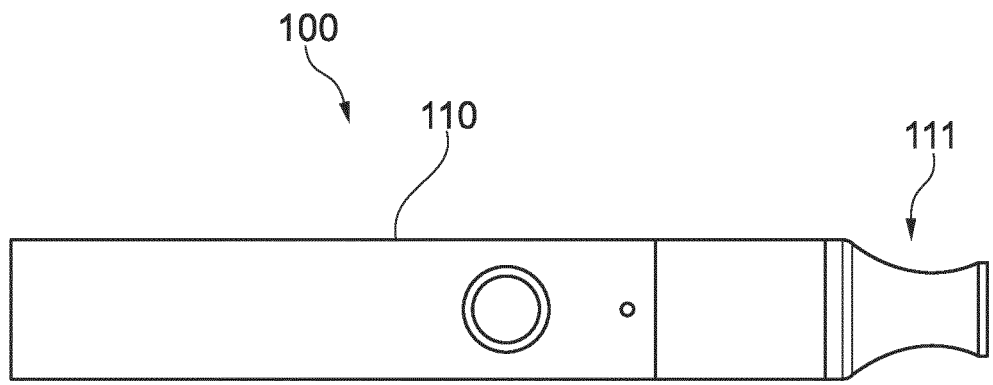
FIG. 1a shows a schematic view of an electronic cigarette, a consumable and a smoking system according an embodiment of the invention.
Figure 1B:
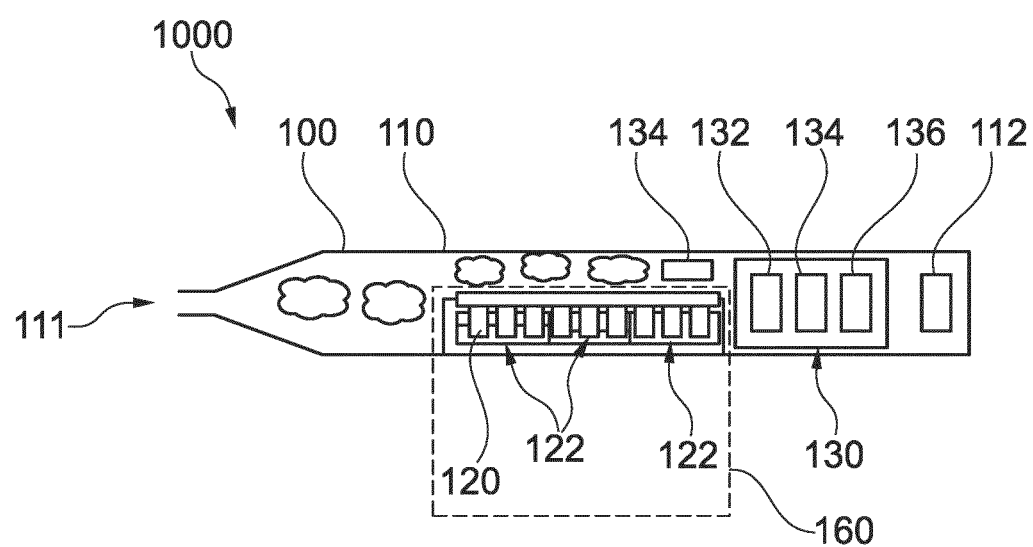

With reference to FIG. 1a and FIG. 1b of the drawings, an electronic cigarette 100 is illustrated.

The electronic cigarette 100 comprises a main body 110, and a mouthpiece portion 111. The mouthpiece portion 11 may form a mouthpiece itself or comprise a connector structure for connecting a mouthpiece ("mouthpiece connector"). Through the mouthpiece portion 111, an aerosol, or vapor, generated by the electronic cigarette 100 can be inhaled.

The aerosol is generated by heating at least one aerosol-generating liquid as will be described in the following. Electrical energy for the heating is provided by a power source 112 of the electronic cigarette 100, for example a battery, preferably a rechargeable battery. As illustrated in FIG. 1b, the electronic cigarette 100 comprises a plurality of liquid reservoirs 122, a regulating arrangement 160, at least one heater 180 (not shown in FIG. 1b), a controller 136 and a timer 134.

The liquid reservoirs 122 are configured to store different liquids. The liquids may comprise different flavours or different active ingredients, such as different nicotine strengths, acids or other. Hence, the aerosol-generating liquids may be different in flavour (e.g. one aerosol-generating liquid may be flavourless or flavour-neutral and the other one may comprise a menthol aroma), different in physical properties (e.g. a vaporisation temperature) and/or different in strength or concentration of the active ingredient. The liquid reservoirs 122 may be configured as replaceable/disposable cartridges 122. The electronic cigarette 100 may also have at least one integrated liquid reservoir in addition to the liquid reservoirs 122 that are provided when the cartridges 122 are inserted into the electronic cigarette 100.

For example, the integrated liquid reservoir may comprise a flavourless aerosol-generating liquid comprising an active ingredient (e.g. nicotine), whereas the liquid reservoirs 122 may comprise aerosol-generating liquid comprising little of the active ingredient or no active ingredient at all. In this way, for example, a user that regularly, or always, intends to inhale an amount of the active ingredient, may fill the integrated liquid reservoir in the electronic cigarette 100 to provide the active ingredient, and may then arrange an assembly of liquid reservoirs 122 in the cartridge 140 that comprise a desired variety of flavours to be mixed into the vapour to be generated together with the vaporised liquid comprising the active ingredient.

As illustrated in FIG. 3, the electronic cigarette 100 may comprise a single cartridge seating 145 configured to receive a cartridge assembly 140 comprising, or consisting of, a plurality of liquid reservoirs 122, e.g. three liquid reservoirs 122 as shown. The cartridge seating 145 may be located at a distal end of a main body (e.g. battery portion) of the electronic cigarette 100 and may be configured as a hollow tube.

In an embodiment, the cartridge assembly 140 may be configured as shown in FIG. 4a through FIG. 4d. Thus the cartridge assembly 140 may comprise a housing 143, a liquid reservoir 122, and may include a fluid transfer element 120. The liquid reservoirs 122 can be provided as separate cartridges 140a, each accommodating a single liquid reservoir 122. The axial cross-section of the cartridges is preferably shaped in relation to the cartridge seating 145 and such that the axial cross sections of a plurality (at least two) cartridges 122 correspond to the axial cross-section of the cartridge seating 145.

The cartridge assembly 140 is configured to take up the space in the cartridge seating 145 when at least two cartridges 140 are mounted together. The housing 143 of the cartridges 140 may therefore have an axial cross-section the shape of a fraction of a circle, preferably a half-circle or a quarter of a circle. It is also possible to combine two quarters of a circle forming a dual cartridge assembly 140 as a single unit.

Figure 5:
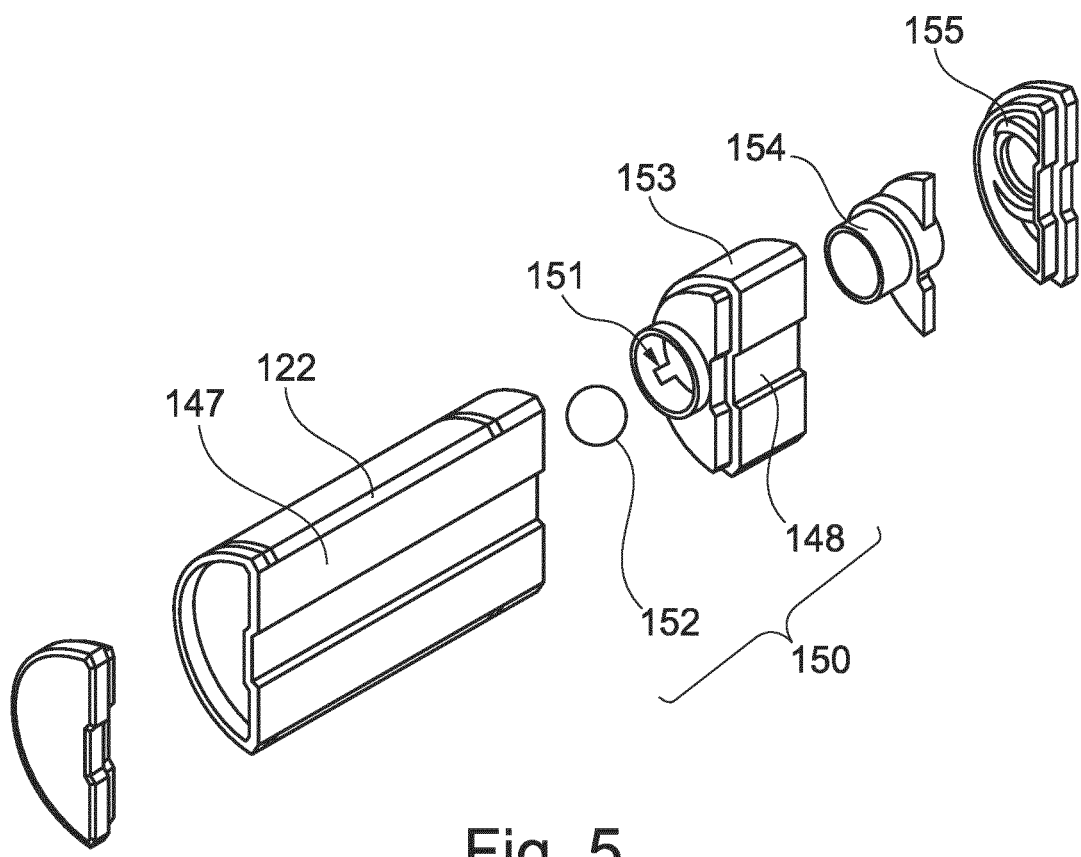
FIG. 5 shows a schematic exploded view of a cartridge according to embodiments of the present invention.

FIG. 5 shows a schematic detail view of the cartridges 140 according to an exemplary embodiment in an exploded view.

As illustrated in FIG. 5, the cartridge 140 may comprise a valve 150 comprising a valve closing member 152 (e.g. in the form of a ball) and a valve seat 153. The valve closing member 152 is biased, by the valve seat 153, to close off a channel 151 so that the liquid supply from the liquid reservoir 122 is closed. The cartridge seating 145 is provided with a fluid transfer element 120. The fluid transfer element 120 is configured to contact a valve seating defined by the circumference of the channel. In another embodiment, heater 180 can be a capillary tube configured to receive liquid from the liquid reservoir and vaporise the liquid into vapour.

Figure 6:
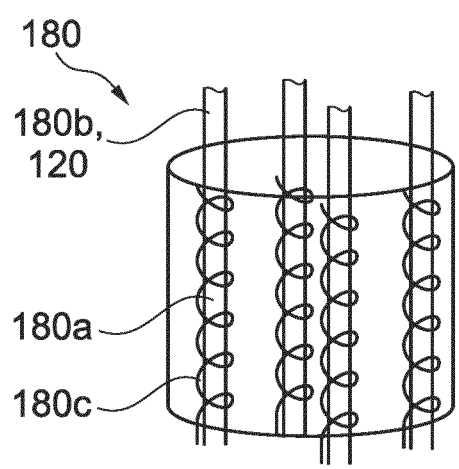
FIG. 6 shows a schematic view of a heater as used in some embodiments of the present invention.

As seen in the alternative embodiments illustrated in FIG. 2a, FIG. 2b and FIG. 6, the fluidic communication between the liquid reservoir 122 and the heater 180 can be established by direct contact with a portion of the heater 180 in the form of a capillary tube.

Hence, as illustrated in FIG. 6, the heater 180 can have the shape of a capillary tube 180a and may be provided with an elongate shape with an absorbing portion 180b and a heating portion 180c. The absorbing portion 180b may thus act as a fluid transfer element 120 for transferring fluid from the liquid reservoir 122 to the heating portion 180c. The temperature of the absorbing portion 180b during use of the electronic cigarette 100 is preferably lower than the temperature of the heating portion 180c during use. Liquid can therefore be transported by capillary action from the liquid reservoir 122 to the heater 180.

Figure 7:
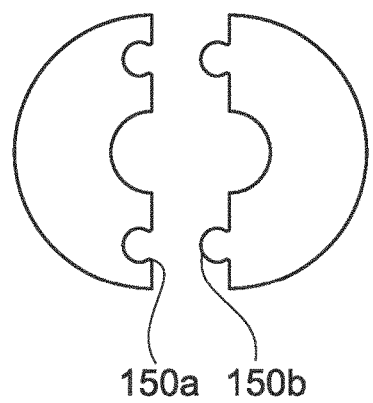
FIG. 7 shows a schematic cross-sectional view of a cartridge according to an embodiment of the present invention.

In a still further embodiment, as illustrated in FIG. 7, the cartridges 140 can comprise a plurality of liquid reservoirs 122. Hence, the axial cross-section of the liquid reservoirs 122 can be shaped such that, put together, their shape corresponds to the shape of the cartridge seating 145. "Corresponding" in this context may be understood to mean that the axial cross-section of the arranged alongside one another essentially fills out the axial cross-section of the cartridge seating 145.

For example, the cross-section of the liquid reservoirs 122 may be shaped as a semi-circle, as a quarter-circle and so on. Preferably, the heater 180 is provided with as many capillary tubes 180a (and corresponding absorbing portions 180b and heating portions 180c) as a maximum number of cartridges 140 which the cartridge seating 145 is configured to accommodate at any time. Alternatively, one heater 180 for each of the maximum number of cartridges 140 may be provided.

In FIG. 6, a heater 180 according to one embodiment is shown that comprises four capillary tubes 180a, each with corresponding absorbing portions 180b and heating portions 180c. Advantageously, the individual heating portions 180c are individually controllable to heat the liquid absorbed by the corresponding absorbing portions 180b. In that way, liquids from different liquid reservoirs 122 may be heated at different times and/or to different temperatures.

That heater 180 is advantageously configured for use with a cartridge seating 145 that is configured to accommodate, at maximum, four different cartridges 140 at the same time, at which time each absorbing portion 180b will be in fluidic contact with one of the four different cartridges 140 each.

It will be understood that the same configuration of the heater 180 is equally suitable for when the same cartridge seating 145 comprises, e.g., three different cartridges 140, wherein one cartridge 140 has a semi-circular cross-section as shown in FIG. 4a to FIG. 4c and FIG. 5, and two cartridges have a quarter-circular cross-section each. Of course, the same applies when the cartridge seating 145 comprises only two cartridges 140 (e.g. both shaped with semi-circular cross-sections, or one with a quarter-circular cross-section and one with a three-quarter-circular cross-section) or when the cartridge seating 145 comprises only one cartridge 140 having a cross-section in the form of a complete circle.

It will also be understood that the heater 180 may also be configured with a different number of capillary tubes 180a, e.g. two, three, five, six, or more capillary tubes 180a with the corresponding number of absorbing portions 180b and heating portions 180c.

In another exemplary embodiment, the cartridge can be configured similar to the embodiment of FIG. 5, but instead of a valve 150 it can comprise a pierceable membrane or a septum sealing its liquid reservoir 122. Such a cartridge is therefore configured to be connected to a fluid transfer element in the form of a piercing member in the cartridge seating 145. The membrane is preferably provided with a high elasticity such that it can reseal when the cartridge 140 is retracted from the piercing member.

As seen in FIG. 5, the cartridge 140 is further provided with a connecting portion 154 and a vapour outlet portion 155. The connecting portion 154 is configured to connect with the main body 110. A vapour groove 147 extends from the connecting portion and a vapour outlet portion. The vapour groove 147 of each cartridge 140 forms a closed vapor channel when at least two cartridges 140 are located inside the cartridge seating 145, i.e. the vapour grooves 147 of a plurality of cartridges 140 may together form the closed vapor channel. The vapor channel is thus configured to enable a flow of vapour from a vaporization chamber 146 located in the proximity of the heater 180. The vaporization chamber 146 may be partially located inside the cartridge 140 and partially located inside the cartridge seating 145, or completely within the cartridge 140 or completely within the cartridge seating 145 of the main body 110.

The cartridge 140 can be provided as a cartomizer and thus comprise an integrated heater 180. A fluid transfer element 120, such as an absorber, for transferring liquid from the liquid reservoir 122 to the heater is in such embodiments integrated into the cartridge 140 as well. Electrical contacts can be provided at the connecting portion 154 of the cartridge. To this effect, the cartridge seating 145 may comprise a plurality of electrical contact pairs configured to provide power to each cartridge heater individually. The electrical contact pairs may be provided having a first contact located at a bottom surface (i.e. a distal or proximal end surface) of the cartridge 140 and a second electrical contact provided around the circumference of the cartridge 140.

The electrical contacts inside the cartridge seating 145 can be provided as resilient contacts configured to connect to first power terminals of the cartomizer cartridge. The resilient contacts establish a good contact between the cartridge and the terminals so that the cartridge can be connected throughout a variable insertion depth in the cartridge seating 145.

The heater 180 can be integrated into the cartridge. Such cartridges are sometimes designated as "cartomizers". Alternatively, similarly as illustrated in FIG. 6, the heater 180 can be formed as a separate atomizer part including a plurality of heaters (e.g., heating portions 180c) and corresponding fluid transfer elements (e.g., absorbing portions 180b). Each fluid transfer element is configured to establish a fluidic connection between one liquid reservoir in the cartridge and one corresponding heater.

The fluid transfer element 120 can be a piercing member arranged at the cartridge seating and configured to penetrate into the cartridge 140 such that a fluidic connection is established between the liquid reservoir 122 and the heater 180.

Figure 4A:
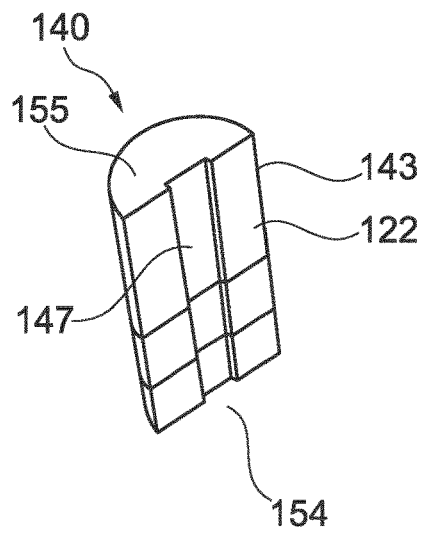
FIG. 4a through FIG. 4d show schematic views of cartridges according to embodiments of the present invention.
Figure 4B:
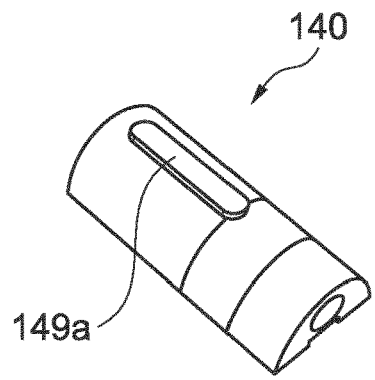
Figure 4C:
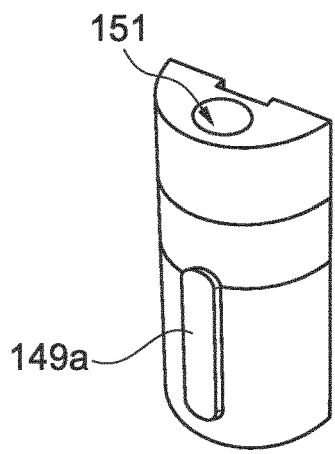
Figure 4D:
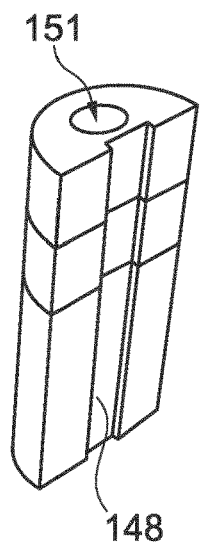
Figure 4D:
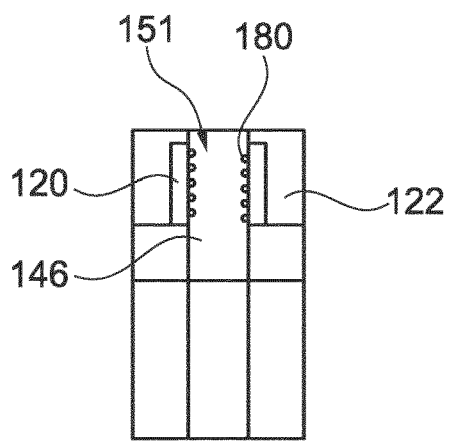

To further enhance the mixing of the vapours from different heaters, the vapour groove 147 (and, as a consequence, also the vapour channel formed by multiple vapour grooves 147) can comprise an airflow diverter 148 configured to create turbulence inside the vapour channel. As seen in FIG. 4c, the airflow diverter 148 can be a protrusion 148 extending in the transverse direction in relation to the vapour groove 147. The protrusion 148 can be provided with a hemispherical shape. Cartridges 140 with different liquids may be provided with protrusions 148 at different axial length of the cartridges to further enhance the turbulence.

The cartridge 140 and the inner walls of the cartridge seating 145 may be provided with cooperating guides 149a, 149b in order to correctly position the cartridge 140 in the cartridge seating 145. The guides can be provided as a keyway 149a on the cartridge 140 and a rail member 149b of the cartridge seating 145, e.g. at an inner surface thereof, and/or a rail member 149c of the mouthpiece portion 111. The cooperating guides extend in the insertion direction of the cartridge 140 into the cartridge seating 145. This enables the electrical contacts of the cartridge 140 to be aligned with the electrical contacts in the cartridge seating 145.

The cartridges 140 may also comprise, as illustrated in FIG. 7, inter-locking connectors 150a, 150b, such that the liquid reservoirs can form, or connect to, a uniform mouthpiece portion 111. The inter-locking connectors may comprise a keyway 150a and a rail member 150b. The interlocking connectors give stability to the composed cartridge. Additionally, the interlocking connectors enable the cartridges to be used directly as a mouthpiece.

Additionally, or alternatively, as seen in FIG. 3, the electronic cigarette 100 may further comprise a mouthpiece portion 111 formed as a sleeve around the cartridges 140. The sleeve is configured to enclose the cartridges 140 and hold them together. To this end, the sleeve may be insertable into, or connectable to, the cartridge seating 145, e.g. by screw threads.

As illustrated in the following FIG. 8a, FIG. 8b, FIG. 9, and FIG. 10, the electronic cigarette 100 may further comprise user controls 170 configured to enable a user of the electronic cigarette 100 to control the mixing of liquids. The liquids may as previously described contain different flavors or different concentrations of ingredients such as nicotine. For instance, the controls may enable to control the amount of liquid that is used from each liquid reservoir 122 to generate the aerosol. In FIG. 8a, FIG. 8b, FIG. 9 and FIG. 10, an embodiment is shown in which the electronic cigarette 100 comprises two different liquids, either by being configured to receive a single cartridge 140 with two different liquid reservoirs 122, by being configured to receive two separate cartridges 140, each of which may comprise a different liquid, and/or the like.

Figure 8:
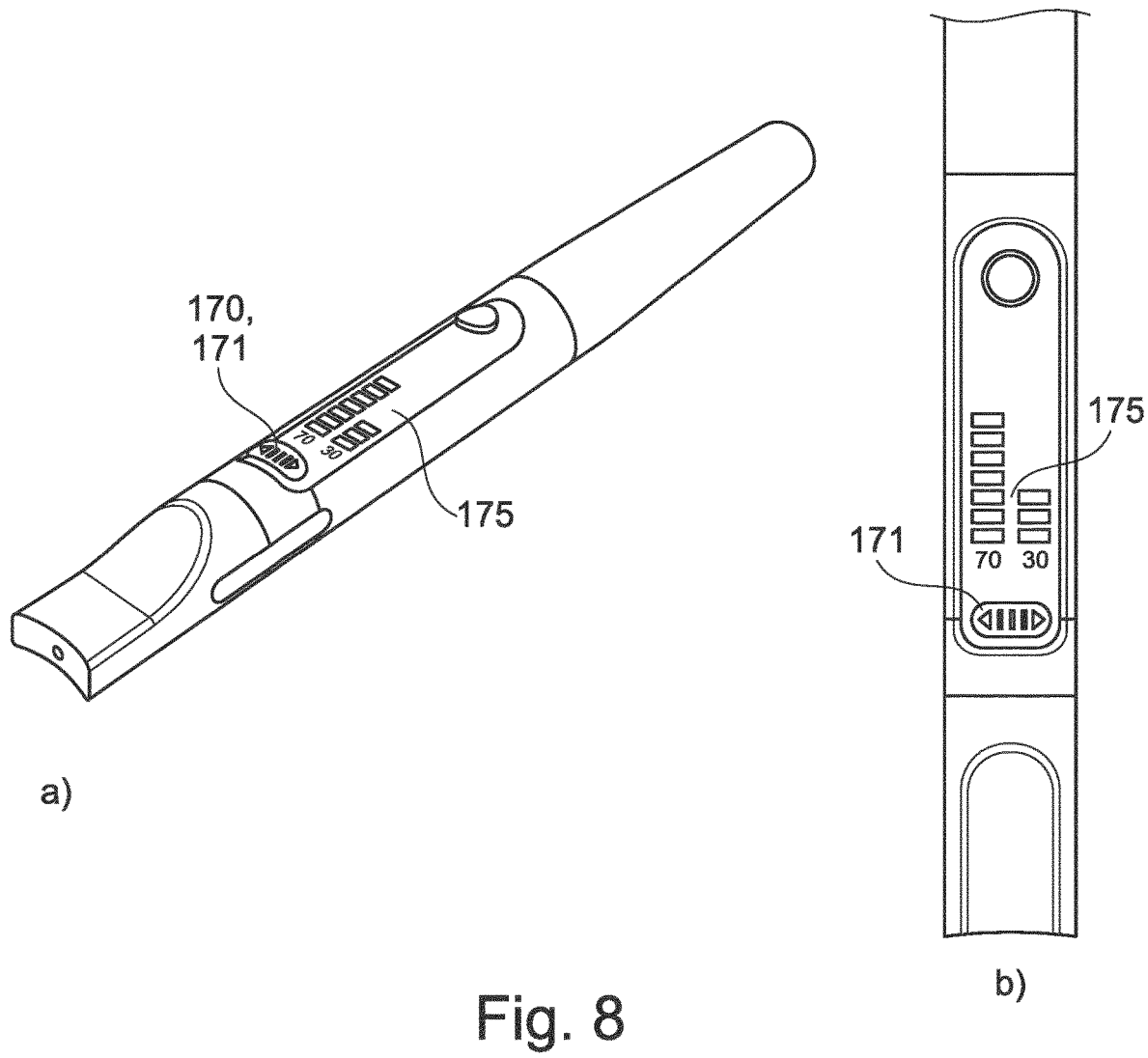
FIG. 8 through FIG. 10 show schematic views of electronic cigarettes according to embodiments of the present invention.

As seen in FIGS. 9a and 9b, the user-control 170 can be in the form of a rocker button 171 or, as shown in FIG. 8, in the form of a set consisting of, or comprising, two separate buttons 172, 173. The electronic cigarette 100 may be configured such that operating one of the rocking ends of the rocker button 171 or one of the two separate buttons 172, 173 results in an amount and/or percentile of a corresponding one of two different liquids being increased in the mix of vapor generated to be inhaled by the user, whereas operating the other rocking end or the other one of the two separate buttons 172, 173, respectively, results in an amount and/or percentile of the other of the two different liquids being increased in the mix.

It should be understood that the set of buttons 172, 173 can be provided with more than three buttons, or the rocker button 171 with more than two rocking ends, wherein in each case the number of buttons/rocking ends preferably corresponds with a maximum number of different liquids and/or different cartridges that are insertable into the electronic cigarette 100. In that way, users can directly set their preferred mix.

The electronic cigarette 100 may further comprise a display 175, i.e. a visual indicator, configured to display (or indicate) the proportion of flavors (i.e. of liquids in the resulting liquid that is vaporized) in the vapor. The display 175 can be formed as light bars that illustrate the relative proportions of the selected liquids.

Figure 9:
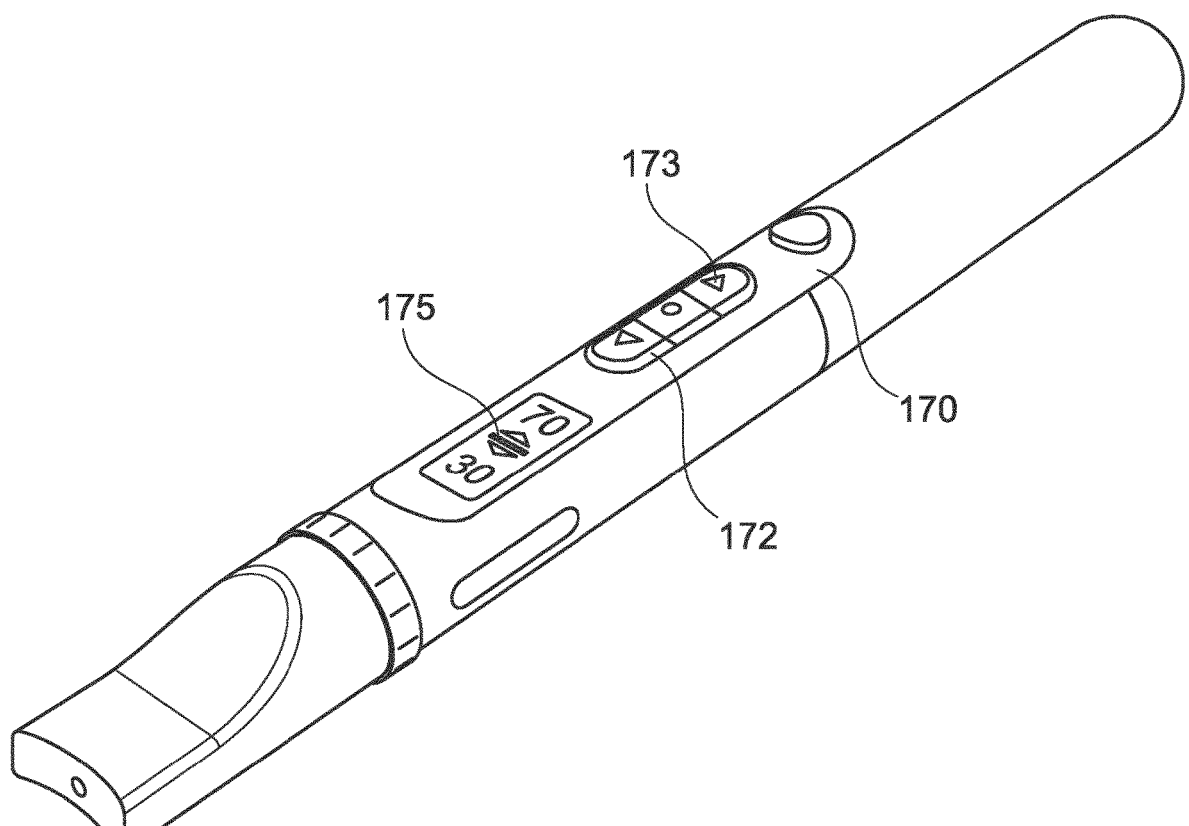
Figure 10:
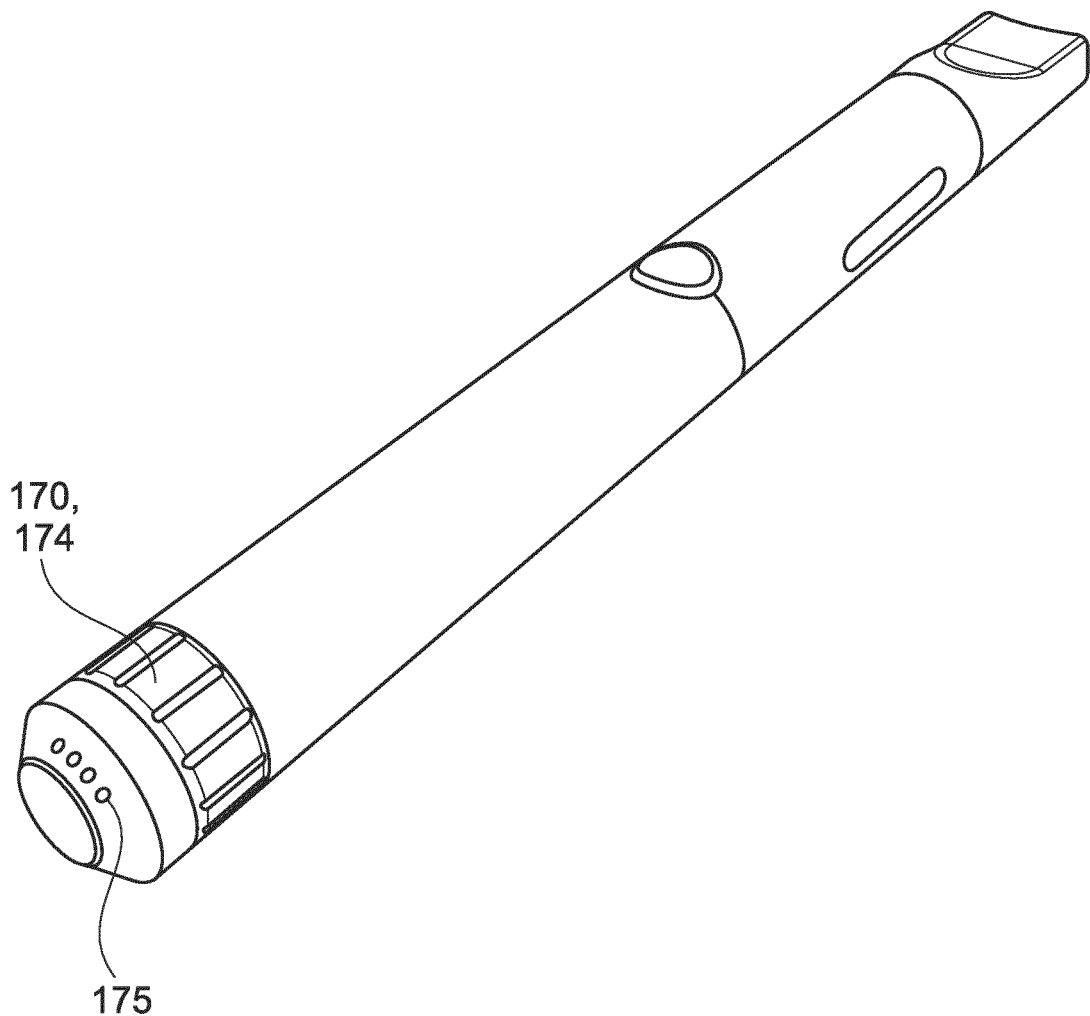

Alternatively, as shown in FIG. 10, the user controls 170 can comprise, or be in the form of, a rotary dial 174. The rotary dial 174 can be positioned on a distal end of the electronic cigarette 100 opposite to the mouthpiece portion 111. When a rotary dial 174 is used, the display 175 can be located within the center of the rotary dial 174. For example, as shown in FIG. 9, the display 175 may comprise a number of light elements (bars, dots, starts, etc.) arranged in a circle, preferably concentrically with the rotary dial 174. This creates a compact user control 170 and display 175 and is positioned outside of the area where the user normally places his fingers so that no accidental modification of the user controls 170 happens during vaping.

However, in a simpler embodiment, the display can be a light source (e.g. a RGB LED) configured to indicate a flavor, flavor mix or nicotine strength of the vapor by different colors and/or intensities of the color(s). Optionally, a plurality of light sources can be used.

The electronic cigarette 100 further comprises a regulating arrangement 160 configured to selectively enable the delivery of liquid from at least one liquid reservoir 122 to at least one heater 180. Hence, the regulating arrangement is configured to open and close the liquid delivery from the different liquid reservoirs 122.

The regulating arrangement may comprise a valve. The valve may comprise a valve body configured to enable and modify the liquid supply from a plurality of liquid reservoirs. The valve body can have a plurality of channels configured to be aligned and disaligned to outlets from the liquid reservoirs and wherein each valve is configured to regulate the flow of liquid from each liquid outlet. For instance the valve body can be rotatable. The regulating arrangement further comprises an actuator, which is connected to the at least one valve and the controller.

Alternatively, the regulating arrangement 160 may comprise a plurality of valves. Each valve may be linked to a unique liquid reservoir or a number of reservoirs.

In another embodiment as illustrated in FIGS. 2b and 6, the regulating arrangement 160 may comprise a plurality of heaters. The heaters may e.g. be realized as Ohmic heating elements, for example as heating wires. The individual heaters of the plurality of heaters may be part of a single heater structure that is divided into a number of individually controllable segments as heaters.

Each heater 180 is connected to at least one fluid transfer element 120 configured to conduct an aerosol-generating liquid from a liquid reservoir 122 to the heater 180 connected to the fluid transfer element 120. The fluid transfer elements 120 may comprise a wick or a needle that delivers the aerosol-generating liquid e.g. by capillary action. The heaters 180 may also be formed integrally with the fluid transfer elements 120, i.e. the heaters 180 may be formed such that they also function as the fluid transfer elements 120.

The liquid reservoirs 122 may in some embodiments be compartments in the housing 110 of the electronic cigarette 100 which are filled, and are preferably refillable, with at least one, preferably more, aerosol-generating liquids.

The electronic cigarette 100 further comprises a control circuitry 130. The control circuitry 130 comprises a memory 132 configured to store at least one program defining a sequence of which liquid reservoir 122 is enabled for liquid delivery a duration of time for the activation. In the embodiment where a plurality of dedicated heaters 180 is used, the control circuitry 130 can therefore control the heater activation times, i.e. which heater is activated when, and a duration of time for the activation. If a valve is used in the regulation arrangement, the control circuitry 130 can control an actuator of said valve in order to position the valve to enable liquid delivery from selected liquid reservoirs 122 to achieve the desired composition of vapour.

The memory 132 may be fixedly integrated into the main body of the electronic cigarette 100 and/or may, partially or completely, be removable from the electronic cigarette 100. For example, the memory 132 could be realized as a computer memory such as a solid-state memory as a memory chip such as a SIM card or in any other known way to store memory. Thus, a memory 132 comprising new and/or updated programs may be inserted into the electronic cigarette 100 by a user. The program may include heating profiles, i.e. information which heater is to be heated to which temperature or temperatures when and how long, or may be usable together with one or more heating profiles stores separately in the memory 132.

In an embodiment, the cartridges are provided with heating elements (e.g., heating coils) having different electrical resistance, wherein at least two different electrical resistances indicate respective different liquid types. The control circuitry 130 of the main body may be configured to measure the electrical resistance of each heating element and to determine the liquid type based on the measured electrical resistance.

The memory 132 (and in particular at least one program stored therein) may also be updated by a user via a user interface. For example, the electronic cigarette 100 may comprise a user interface (a touch screen, a number of manipulators such as buttons and/or dials and the like, etc.) with which the user may change some or all parameters of one or more of the programs stored in the memory 132.

Preferably, the electronic cigarette 100 comprises a wire bound or wireless interface through which a computing device of the user, such as a mobile phone, a tablet, a laptop or the like, may be, preferably wirelessly, connected to the memory 132 in order to change parameters of one or more of the stored programs, to remove programs from the memory 132 and/or to add new programs to the memory 132. The interface is preferably configured to enable the user, when changing parameters, to extend or shorten a duration of a heater activation time of one or more of the heaters and/or shift the heater activation time of at least one heater forward or backward in time with respect to at least one other heater activation time. The interface may alternatively give the user a list of options such as "stronger taste" or "fresher" and may then translate the user's settings into appropriate settings within at least one program and/or heating profile.

By the interface, data may be transmitted to the computing device indicating which type of aerosol-generating liquid is present in each of the liquid reservoirs 122, or, more directly, which type of aerosol-generating liquid is currently being arranged to be supplied to which heater. In this way, the user knows which type of aerosol-generating liquid will be affected when the user changes the heater activation time of the corresponding heater in any way.

The control circuitry 130 also comprises a timer 134 configured to control the enablement of each liquid reservoir 122 according to the selected program from the memory 132. The timer 134 can therefore control the time the valve is in each position or regulate the time during which each heater is activated, in particular to monitor how long each heater is activated (i.e. measure the heater activation time) and to output a corresponding heater activation time signal. The heater activation time signal may indicate an amount of time e.g. in seconds (or milliseconds or the like) or in a number of puffs.

The control circuitry 130 further comprises a controller 136 configured to selectively control the activation of each heater according to the at least one program on the memory 132 and/or according to at least one heating profile. The timer 134 may also be integrated into the controller 136.

The program may comprise two or more heaters being activated at the same time and/or two or more heaters being activated at different times. The activation times of two or more heaters may overlap, in particular for at least 10%, at least 30%, at least 50%, at least 70% or at least 90% of either activation time. The heater activation times for each heater may have the same duration. Alternatively, some heater activation time may have different durations from one another. In some embodiments, all of the heaters may have different heater activation times.

One important characteristic of the electronic cigarette is a temperature to which the consumable is heated to generate the aerosol. This temperature is also referred to as a "vaping temperature". The vaping temperature can have a significant impact on the user's vaping experience for multiple reasons. Excessive heating can increase the temperature of the inhaled vapour to an uncomfortable level, cause faster consumption of the consumable, in particular of the aerosol-generating liquid, and may cause more rapid degradation of the components of the electronic cigarette. Moreover, an optimal vaping temperature may be different for differently composed consumables, as different components of the e-liquid may vaporise and/or release flavours at different temperatures.

Each heater may be provided with a temperature sensor configured to sense a temperature of the heater and to provide an according heater temperature sensor signal to the controller 136. Based on that heater temperature sensor signal, the controller 136 may control the individual vaping temperatures of the heaters which may be different from one another. The electronic cigarette 100 may be configured such that the vaping temperatures of the heaters are—at least partially—different and fixed. In that case, the aerosol-generating liquid can be arranged according to their respective vaping temperature in the cartridge 140, as will be described in the following. In other embodiments, the vaping temperature of each heater may be individually controllable by the controller 136, e.g. based on information about the aerosol-generating liquid being currently supplied to each individual heater, specifically based on information about the vaping temperature of said aerosol-generating liquid, for example as described later with respect to a data storage of the cartridge 140.

When the heaters are activated at different times and/or for different heater activation times, then advantageously the vapour composition of the vapour varies in time according to the program stored on the memory 132.

In FIG. 1 and the following FIG. 2a and FIG. 2b, an embodiment is illustrated according to which the electronic cigarette 100 is configured to receive a consumable, in particular a cartridge 140, comprising at least one liquid reservoir 122, and preferably at least two liquid reservoirs 122. More preferably, the at least two liquid reservoirs 122 of the cartridge 140 comprise two different aerosol-generating liquids, i.e. aerosol-generating liquids of different composition.

The (at least one) liquid reservoir integrated into the electronic cigarette 100 may therefore be larger than one, or all, of the liquid reservoirs of the cartridge 140 or may even be larger than the cartridge 140 itself.

In the following, the case will be described in more detail in which there is no liquid reservoir integrated into the electronic cigarette 100. The embodiment of FIG. 1 is illustrated also with respect to FIG. 2a and FIG. 2b.

FIG. 2a shows a schematic perspective view of the fluid transfer elements 120 of the electronic cigarette 100 and of a sealed cartridge 140 comprising liquid reservoirs 122. The liquid reservoirs 122 can be provided on a support 123 configured to group the plurality of reservoirs 122 together.

FIG. 2a shows a cartridge 140 with three different liquid reservoirs 122, each of the same size, that are sealed so that no aerosol-generating liquid may spill. The three different liquid reservoirs 122 are arranged next to each other, separated by a respective divider wall, and are rectangular in shape. Preferably, each liquid reservoir 122 comprises an aerosol-generating liquid different from the other liquid reservoirs 122 such that the cartridge 140 carries, in this example, three different aerosol-generating liquids.

As is also evident from FIG. 2a, when the cartridge 140 is completely and correctly inserted into, or attached to, the electronic cigarette 100, then the fluid transfer elements 120 align in a predefined way with the cartridge 140. Preferably, each fluid transfer element 120 is aligned with exactly one liquid reservoir 122 of the cartridge 140. In this way, a maximal variety of flavours may be provided to the user.

The present invention thus also provides a cartridge 140 comprising a plurality of liquid reservoir 122 arranged and configured such that, when the cartridge 140 is inserted into, or attached to, the electronic cigarette 100 in a predefined way, each of the liquid reservoirs 122 of the cartridge 140 is aligned according to a predefined way with at least one, preferably with exactly one, fluid transfer element 120 of the electronic cigarette 100.

FIG. 2b illustrates that the heaters 180 may each be formed with a piercing member, in particular a needle comprising a capillary tube, which act as fluid transfer elements 120 by capillary action after they have pierced a seal or membrane protecting the liquid reservoirs 122 of the cartridge 140.

The present invention accordingly also provides a smoking system 1000 comprising an electronic cigarette 100 according to the present invention and a cartridge 140 according to the present invention configured to align with each other in the way described in the foregoing.

In the example of FIG. 1 and FIG. 2a, the cartridge 140 has only three liquid reservoirs 122 which are arranged such that each liquid reservoir 122 is aligned with six of the fluid transfer elements 120. In other cartridges 140 for the same electronic cigarette 100, the apportionment may be different.

In the example shown in FIG. 1 and FIG. 2a, the cartridge 140 is further provided with a sealing 142 or packaging which is configured and arranged to seal off one or more of the liquid reservoirs 122 of the cartridge 140 to prevent leakage. For example, the cartridge 140 may be formed with the plurality of liquid reservoirs 122 which my then be filled with at least two different aerosol-generating liquids, and then a sealing foil may be placed and fixed over the liquid reservoirs 122 to seal them.

In the embodiment of FIG. 1 and FIG. 2a, the fluid transfer elements 120 of the electronic cigarette 100 are realized as comprising, or consisting of, piercing members 124 configured to be able to pierce the sealing or packaging, which seals the individual liquid reservoirs 122 of the cartridge 140. The piercing of the liquid reservoirs 122 may occur coincident with the cartridge 140 being fully and correctly inserted into a receiving cavity of the electronic cigarette 100. The piercing members may be configured as hollow tubes with sharpened ends (e.g. as hollow needles) through which aerosol-generating liquid is drawn via capillary action from the liquid reservoirs 122. In some embodiments, the fluid transfer element 120, the piercing member 124 and the corresponding heater may be realized as a single element, i.e. the heaters may function as heaters, as fluid transfer elements and as piercing members.

The receiving cavity of the electronic cigarette 100 may comprise the piercing members 124 which are arranged such that, when the user inserts the cartridge 140 for the first time into the receiving cavity, the user pushes the sealing or packaging of the cartridge 140 against the piercing members 124 until the piercing members 124 pierce the sealing or packaging of the liquid reservoirs 122 of the cartridge 140. In other embodiments, the piercing members 124 may be moveable between a retracted and an extended position, wherein the piercing members 124 pierce the sealing 142 of the cartridge 140 only when they are in the extended position. Then, the cartridge 140 may be inserted into the electronic cigarette 100 without its sealing 142 being pierced automatically. The contents of the cartridge 140 may thus remain fresh longer, i.e. until the user actually wants to start the vaping session, at which point the user will extend the piercing members 124 using an actuating member such as a push button or a lever.

When the piercing members 124 have pierced the sealing 142 or packaging of the liquid reservoirs 122, the fluid transfer elements 120 conduct the aerosol-generating liquids within the liquid reservoirs 122 to the respective heaters to be heated for the generation of the vapour.

The cartridge 140 may be provided with a data storage that comprises information about which kind of aerosol-generating liquid is contained in each of the liquid reservoirs 122 of the cartridge 140. In other words, the information may indicate which aerosol-generating liquid of the cartridge 140 is deposited in which liquid reservoir 122 and/or which composition it has. The information may also indicate an optimal vaping temperature of each aerosol-generating liquid, or information that allows the controller 136 to determine the vaping temperature for each aerosol-generating liquid via a database, a look-up table, an internet link or the like. The controller 136 may then control each heater to function at the respective vaping temperature.

The information may be transmitted from the data storage of the cartridge 140 to the electronic cigarette 100, e.g. to the controller 136 or the memory 132 so that the controller 136 knows which heater is to be activated in order to produce vapour from a certain aerosol-generating liquid contained in one of the liquid reservoirs 122 of the cartridge 140. In this way, when two types of cartridge 140 e.g. comprise, among others, the same aerosol-generating liquid but have arranged the liquid reservoir 122 containing said aerosol-generating liquid at different positions of the cartridge 140, the controller 136 will be aware of the true position of the aerosol-generating liquid and control the heaters accordingly, based on at least one program and/or heating profile.

The information from the cartridge 140 may be transmitted wirelessly from the cartridge 140 to the electronic cigarette 100, e.g. by RFID or Bluetooth or the like, or a contact interface may be provided, by which the controller 136 is able to determine the contents and/or positions of the aerosol-generating liquids contained in the liquid reservoirs 122 of the cartridge 140.

The information for the cartridge 140 may also be printed as a code segment on a part of the cartridge 140 such as on a surface of the cartridge 140. That code segment may thus act as a data storage of the cartridge 140. The code segment may be read by the electronic cigarette 100 electrically and/or optically, i.e. by an electric and/or optic reading device of the electronic cigarette 100.

Alternatively, the data storage on the cartridge may be in the form of a memory, configured to store a plurality of programs. The programs may include different combinations and sequences of the liquids in the cartridge. To this effect, the main body can be configured to select one of the programs included on the memory. The cartridge may further comprise an indicia or a description of the programs available on the cartridge to inform the user about the flavour characteristics of the program.

Hence, the data storage of the cartridge 140 may also comprise a complete program for the controller 136 to follow. Thus, the controller 136 may be configured to automatically select and follow a program from the data storage. For example, a specific cartridge 140 may be designed to offer the user a flavour journey akin to a multi-course meal, with carefully blending and varying vapour compositions over time. A single program for such a flavour journey may be stored in the cartridge 140 and be automatically followed by the controller 136 of the electronic cigarette 100, or there may be a plurality of programs stored on the cartridge 140, from which the controller 136 will automatically select one program based on e.g. a preference of the user, a setting of the electronic cigarette 100 (for example a desired time duration of the flavour journey indicated by the user via the user interface), a time of the day, a time in the circadian rhythm of the user, a prescribed drug dosage, sensor data and/or personal data, as will be explained in more detail in the following.

Information about the contents of the cartridge 140 may be displayed to the user via a display of the electronic cigarette 100 and/or, via the optional interface described in the foregoing, by a mobile device of the user, e.g. in an app of a smartphone. The user is thus able to compose a personalized flavour program, making selections from the aerosol-generating liquids available from a certain type of cartridge 140 which is, e.g., automatically determined or which the user has input into the electronic cigarette 100 by the user interface. Instead of a single cartridge 140, the electronic cigarette 100 may be configured to receive a plurality of cartridges 140, each providing information about its contents to the controller 136 in one of the ways discussed in the foregoing.

Similarly, the electronic cigarette 100 may be configured to let the user, e.g. using the user interface, input what type of flavour program the user would like to experience, for example by making a selection from flavours provided as options from a server. The user may then be informed, by a display of the electronic cigarette 100 and/or by a mobile device connected to the electronic cigarette 100 by the interface, which cartridge the user would have to insert into the electronic cigarette 100 so that the electronic cigarette 100 is able to produce the desired flavour program.

The flavour program may also be set partially, or completely, automatically. The electronic cigarette 100 may comprise at least one sensor that is configured to sense an environment condition and/or a property or a state of the user, and to determine, or adjust, the program of the electronic cigarette 100 accordingly.

For example, a sensor and/or a determining routine of the controller 136 may determine a circadian rhythm of a user and transmit data relating to said rhythm to the controller. The controller may then consult the memory 132 which may comprise a database linking sections of the circadian rhythm to parameters of vapour compositions. The database may be a general database for all users, or may be personalized for one or more individual users.

The determining of the circadian rhythm may be aided and/or performed by the determining routine running on the controller 136 which may keep track of time and enable the user to provide information to help synchronise the controller 136 to the user's circadian rhythm. The determining routine may be configured to determine the circadian rhythm also based on the previous usage of the device which may be determined and stored by the controller 136 within the memory 132. The determining routine may also receive measurements and/or personal data from a mobile device of the user, such as from a smart watch or a smart phone and determine the circadian rhythm based on said measurements and/or personal data. The personal data may include e.g. sleep patterns or patterns of other activities of the user.

For example, a user may prefer vapour compositions that are perceived as "mild" after waking up in the morning, may prefer stronger tastes during the day and may prefer more balanced vapour compositions in the evening. The electronic cigarette 100 may comprise a clock configured to provide the controller 136 with the time of the day, and the controller 136 may be configured to adapt the vapour composition of a program and/or to select a program based on the time of the day.

Combined with the sensor and/or routine for determining the circadian rhythm of the user, the electronic cigarette 100 may thus be able to always provide the user with the most desired vapour composition whenever the user activates the electronic cigarette 100. For example, the flavour and/or smell sensitivity of most users varies over time, in particular with the circadian rhythm. A program may be configured such that the perceived flavour experience for a user is constant over time, e.g. by increasing a ratio of flavour-carrying aerosol-generating liquids with respect to flavourless or flavour-neutral aerosol-generating liquids when the flavour and/or smell sensitivity of the user is comparatively lower, and to reduce said ratio when the sensitivity of the user is higher.

The electronic cigarette 100 may be configured to perform a test with a user in which it provides different flavour intensities to a user (preferably at different times of the day and/or different times with respect to the circadian rhythm of the user) and requires an input of the user characterizing the perceived strength of flavour. The controller 136 may be configured to select and/or adapt a program stored in the memory 132 based on results of the test.

As another example, when the electronic cigarette 100 is used to administer a drug with an unpleasant smell and/or taste, the vapour composition may be configured such that that smell and/or taste is hidden from the user or neutralized by the vapour composition.

The internal clock and/or the sensor for determining the circadian rhythm may also be used to ensure, or facilitate, the prescription of a drug to a user according to a dosage regime. For example, the user may have a prescription for a comparatively lower dosage of the drug during the morning (and/or during a number of hours after waking up) and a prescription for a comparatively higher dosage of the drug during the afternoon (and/or during a number of hours after the previous period, or before going to sleep). The electronic cigarette 100 may thus be employed as a device for delivering a pre-set drug dosage over time to a user. The program controlling the addition of the drug to the vapour composition may be put together, or approved, by a physician and may preferably be unalterable by the user.

The internal clock may also be configured to provide a current date, and the program may comprise a program for weaning off of a drug in which the dosage of the drug is e.g. reduced every day. The corresponding program may be configured to compensate the reduced amount of the drug by a corresponding change in another component of the vapour composition. For example, a reduced amount of nicotine could be compensated by an increased amount of an aerosol-generating liquid that has a tobacco flavour or that creates a sensation close to the sensation of smoking actual tobacco. Similarly, if a certain active ingredient produces a certain sensation for the user when inhaled, a reduced amount of said active ingredient could be compensated by an increased amount of an aerosol-generating liquid that produces the same sensation for the user. The user may therefore have the impression that the drug content is not reduced at all.

The electronic cigarette 100 may in some advantageous embodiments also comprise a particle sensor such as a food molecule sensor. In this way, the vapour composition can automatically be set by the controller 136 based on e.g. a previous consumption of a user and/or on a chemical balance (e.g. acidic/basic) within the mouth of the user. Preferably, the particle sensor is arranged at the mouthpiece 111 of the electronic cigarette 100 or at a connector for connecting a mouthpiece to the electronic cigarette 100. The particle sensor is preferably arranged and configured to detect molecules in the saliva of the user, e.g. using molecularly imprinted polymers.

The corresponding settings may be stored in the memory 132 by the user according to the user's preferences. For example, a user may prefer vapour compositions with a cooling effect or a cooling sensation after having consumed a spicy meal. The particle sensor may be configured to detect capsaicin in the user's breath and/or saliva and select a "after spicy meal" program or to choose a "after spicy meal" setting within a program. Similarly, the taste and/or smell sense of the user may be dulled after a particularly flavour-intensive meal such that the vapour composition may have to be adapted to also include stronger flavours in order to counteract the effect.

The cartridge 140 may also comprise an aerosol-generating liquid acting as a palate cleanser which helps the user to better sense flavours after it has been inhaled. The controller 136 may be configured to automatically add a heater activation time for a heater arranged to heat the palate-cleansing aerosol-generating liquid before all programs based on a sensor signal of the particle sensor. Additionally, or alternatively, the memory 132 may comprise a special palate-cleansing program that comprises a heater activation time for the palate-cleansing aerosol-generating liquid. The controller 136 may be configured to automatically select the palate-cleansing program based on the sensor signal of the particle sensor and/or the user may be able to manually activate the palate-cleansing program.

The particle sensor may also be configured to detect bad odours in the breath or mouth of the user, and to choose a vapour composition or a program to counter, or lessen, the detected bad odours specifically. Specifically, a vapour composition set according to other criteria (e.g. personal preference, time of the day and/or contents of the cartridge 140 and the like) may be adapted to include, in addition, an agent designed to counteract the detected bad odour or odours in the breath of the user. Such an addition of a breath-improving agent to the vapour composition may be triggered by measuring a concentration of a specific chemical substance over a predefined threshold, and may last until the measured concentration has fallen below a threshold, which may be the same or different (in particular lower) than the first threshold.

A typical vaping session may start with the user inserting a cartridge 140 into the electronic cigarette 100 fully and correctly (e.g. closing the electronic cigarette 100 thereafter) such that the fluid transfer elements 120 can or will conduct the aerosol-generating liquids from the cartridge 140 to the heaters of the electronic cigarette 100. The user then turns on the electronic cigarette 100 and places the mouthpiece on the user's lips.

The controller 136 may then apply a flavour selection algorithm to determine an initial program, i.e. an initial vapour composition and a temperature setting to use. The initial vapour composition may comprise only vapour from a single aerosol-generating liquid but may also comprise vapours from a plurality, or even all of, the aerosol-generating liquids available from the cartridge 140.

During the course of the vaping session, the controller 136 may adjust the vapour composition by activating and/or deactivating different heaters and/or controlling the heaters to function at different vaping temperatures based on a chosen flavour program and/or on any of the inputs as has been described in the foregoing, e.g. based on sensor data and/or personal data about the user (circadian rhythm, composition of the user's breath or saliva, time of the day, current date and so on) and/or data from the data storage of the cartridge 140. Of course, the user may also be allowed to manually change some or all of the setting of the program using a user interface of the electronic cigarette 100. For instance, the user control may be used to skip over a flavor that the user does not like and advance to the next flavor. The memory 132 can register that the user did not like the sequence and remove it from the program.

Although specific embodiments of the invention are illustrated and described herein, it will be appreciated by those of ordinary skill in the art that a variety of alternate and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

LIST OF DRAWING SIGNS 100 electronic cigarette
110 main body
111 mouthpiece portion
112 power source
120 conducting member
122 liquid reservoir
123 support
124 piercing member
130 control circuitry
132 memory
134 timer
136 controller
140 cartridge
142 sealing
143 housing
145 cartridge seating
146 vaporization chamber
147 vapor groove
148 airflow diverter
149a keyway
149b rail member
149c rail member
150 valve
150a rail member
150b keyway
151 channel
152 closing member
153 valve seat
154 connecting portion
155 vapor outlet portion
160 regulating arrangement
170 user controls
171 rocker button
172 button
173 button
174 rotary dial
175 display
180 heater
180a capillary tube
180b absorbing portion
180c heating portion
1000 smoking system

The invention claimed is:

1. An electronic cigarette comprising:
a plurality of liquid reservoirs configured to store different liquids,
at least one heater, wherein each of the plurality of liquid reservoirs is fluidically coupled to the at least one heater,
a regulating arrangement configured to selectively enable delivery of liquid from at least one of the plurality of liquid reservoirs to the at least one heater,
a memory configured to store at least one program defining which of the plurality of liquid reservoirs is enabled for liquid delivery to the at least one heater and a duration of time for activation,
a controller configured to selectively control enablement of each of the plurality of liquid reservoirs according to the at least one program on the memory, and
a timer configured to regulate a time during which each of the plurality of liquid reservoirs is enabled,
whereby the electronic cigarette is configured to produce a vapour with variations in its composition over time during the course of a vaping session, and
wherein the at least one program is based on a sensor input, wherein the sensor input relates to at least one of a circadian rhythm of a user, a breath of the user, saliva of the user, an odour in a mouth of the user.

2. The electronic cigarette according to claim 1, wherein the regulating arrangement comprises at least one valve.

3. The electronic cigarette according to claim 1, wherein the regulating arrangement comprises the at least one heater, and the at least one heater includes a plurality of heaters, and wherein each of the plurality of liquid reservoirs is fluidically coupled to one of the plurality of heaters.

4. The electronic cigarette according to claim 3, wherein each of the plurality of liquid reservoirs is coupled to a dedicated one of the plurality of heaters.

5. The electronic cigarette according to claim 3, wherein the controller is configured to selectively control activation of each of the plurality of heaters according to the at least one program on the memory.

6. The electronic cigarette according to claim 3, wherein the timer is configured to regulate the time during which each of the plurality of heaters is activated.

7. The electronic cigarette according to claim 3, wherein at least two of the plurality of heaters can be activated at separate times or at least two of the plurality of heaters can be activated at the same time.

8. The electronic cigarette according to claim 1, wherein the plurality of liquid reservoirs comprise liquids of different nicotine strength and wherein the variations in vapour composition include a variation in nicotine strength.

9. The electronic cigarette according to claim 1, wherein the plurality of liquid reservoirs comprise liquids of different flavors and wherein the variations in vapour composition include a variation in flavor.

10. The electronic cigarette according to claim 1, wherein the plurality of liquid reservoirs are provided on a support forming a unitary cartridge assembly and wherein the at least one program is located on the memory on the cartridge assembly.

11. The electronic cigarette according to claim 1, wherein the at least one program is located on the memory on a main body of the electronic cigarette.

12. The electronic cigarette according to claim 1, wherein the at least one program contains different heating profiles in order to achieve different flavour strengths.

13. The electronic cigarette according to claim 1, wherein the at least one program comprises a set of different heating profiles, and wherein each of the set of different heating profiles is linked to a specific composition and/or flavour.

14. The electronic cigarette according to claim 1, wherein the at least one program can be created by a user.

15. The electronic cigarette according to claim 1, wherein each of the at least one heater is in the form of needles each with a capillary tube.

16. The electronic cigarette according to claim 1, wherein each of the at least one heater is moveable between a retracted position and an extended position.

17. A cartridge assembly for an electronic cigarette, the cartridge assembly having a plurality of liquid reservoirs formed as separate compartments, wherein the cartridge further comprises a memory configured to store at least one program, wherein the at least one program comprises instructions which enable a regulating arrangement in the electronic cigarette to produce a vapour with variations in its composition over time during the course of a vaping session, and wherein the at least one program is based on a sensor input, wherein the sensor input relates to at least one of a circadian rhythm of a user, a breath of the user, saliva of the user, an odour in a mouth of the user.

* * * * *